United States Patent [19]

Chester

[11] Patent Number: 4,481,947
[45] Date of Patent: Nov. 13, 1984

[54] ENDOTRACHEAL TUBE RETRACTOR

[76] Inventor: Martin H. Chester, 25310 Tierra Grande, Carmel, Calif. 93923

[21] Appl. No.: 121,620

[22] Filed: Feb. 14, 1980

[51] Int. Cl.³ .............................................. A61B 17/00
[52] U.S. Cl. .................................... 128/303 R; 128/20
[58] Field of Search .......................... 128/20, 303 R, 3

[56] References Cited

U.S. PATENT DOCUMENTS 3,701,348 10/1972 Nauara .................................. 128/20

FOREIGN PATENT DOCUMENTS 182293 7/1966 U.S.S.R. .......................... 128/303 R

OTHER PUBLICATIONS

Chas. Truax Greene & Co. Catalog.

J.A.M.A. "Molded Lucite Surgical Instruments", vol. 149, No. 11, Jul. 12, 1952, pp. 1018-1019.
Codman General Surgical Instruments Catalog Cover Page, pp. 83 and 193, (1973), Found in A.U. 335 V.
Mueller & Co., Catalog p. 232, (1929).
Scanlan-Morris Co. Brochure, pp. 2-4.
Murray-Baumgartner Surgical Instrument Co. Catalog, p. 113, (1934).
Stille Stainless Steel Retractors Pamphlet, (1939), pp. 1-4.

Primary Examiner—Michael H. Thaler

[57] ABSTRACT

An endotracheal tube retractor used to facilitate endotracheal intubation and endotracheal tube placement is provided with an angled handle and a scoop-shaped blade for engaging and manipulating an endotracheal tube. The retractor may be used in both the direct and blind orotracheal and nasotracheal intubation techniques.

3 Claims, 3 Drawing Figures

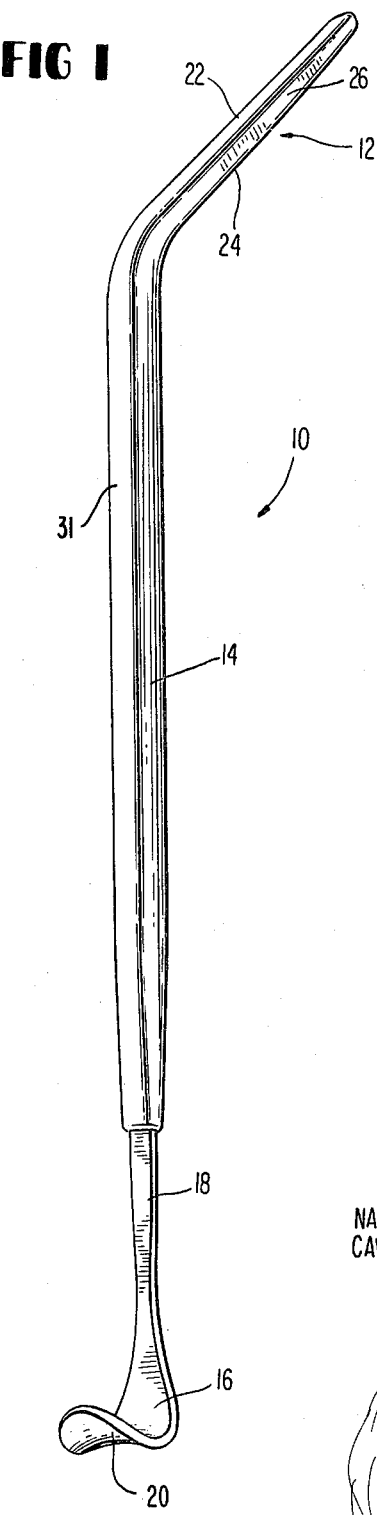
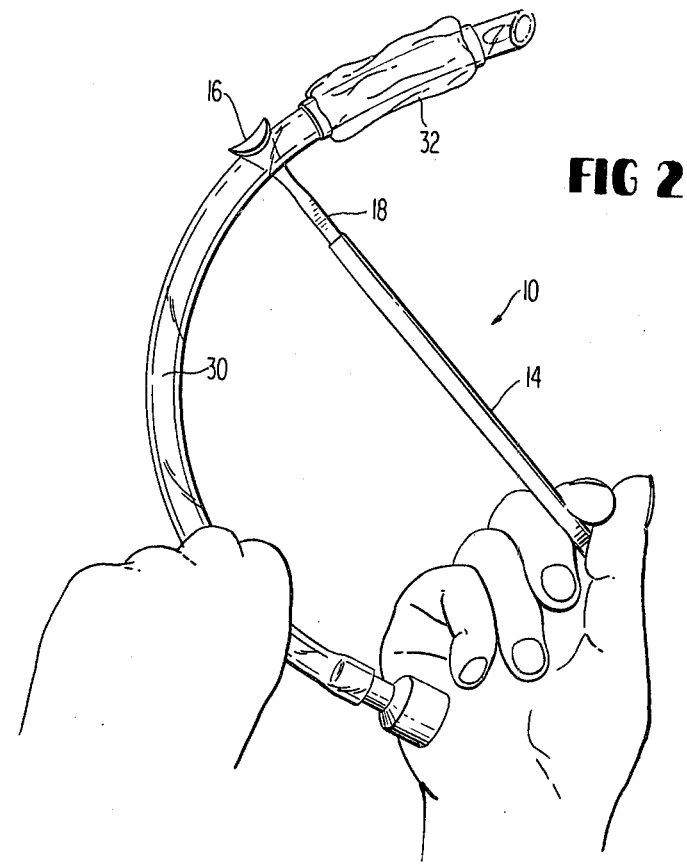
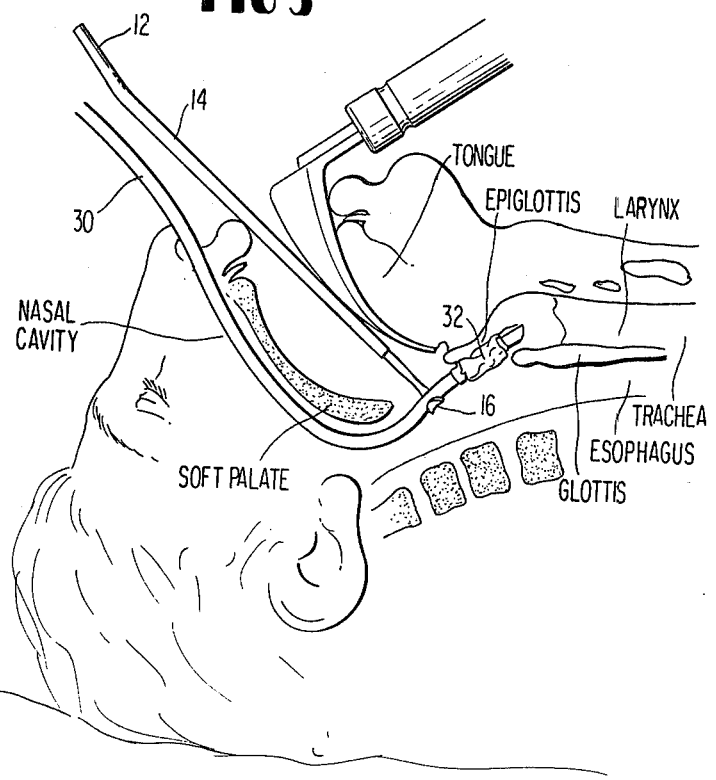
FIG 1
FIG 2
FIG 3

ENDOTRACHEAL TUBE RETRACTOR

BACKGROUND OF THE INVENTION

1. Field of the Invention

The invention relates generally to the field of endotracheal intubation, and more particularly, to an endotracheal tube retractor useful in the intubation of patients under either direct vision or blind techniques.

2. Description of the Prior Art

The intubation of patients is a technique well known in the anesthesia and medical arts, and involves the insertion of an endotracheal tube into the trachea through either the nose or mouth. In the direct technique, the tip of the endotracheal tube is observed with a laryngoscope as the tube progresses down the posterior pharynx into the glottis, through the vocal cords and into the trachea. During nasotracheal intubation, it is often necessary to guide the endotracheal tube into the glottis with the aid of forceps. In intubation of this type, the visible end of the endotracheal tube is grasped with the forceps, and the practioner controls the direction of the tip of the tube in order to glide it into the glottis and through the vocal cords.

In the blind technique, the tube direction is changed by flexion, extension, or rotation of the head, as the blind application of forceps is extremely hazardous and is of very limited value in facilitating blind intubation.

U.S. Pat. No. 3,701,348 to Navara discloses a tool used for pathological procedures, such as the opening of the skull. To this end, the device of Navara is provided with a relatively flat elongated center portion, a flat chiseled portion formed on one end of the center portion, and a curved retractor portion formed on the other end of the central portion. As seen in FIG. 1 of the patent, the retractor portion 17 comprises an inwardly curved member and is of about the same length as the chisel portion 15. In use, a cut is made in the skull by a suitable high velocity saw. The chiseled portion 15 is inserted into the groove made by the saw blade, and is then laterally moved to separate the parts of the skull by prying. The retractor portion 17 is then used to hook an edge of the severed portion, and to remove the same. However, while the device disclosed by Navara may have certain utility as a skull retractor, it is much larger than anything which would be usable for tracheal work. Furthermore, the center portion of the Navara device is flat, and is therefore unsuitable for gripping by the hand of a practitioner where delicate work is involved.

The V. Mueller & Co. Catalogue (1929) at page 232 discloses two types of retractors for use in tracheal work. The retractor A8535, known as Shurly's retractor, consists merely of a flat length of sheet steel with a bend in one end. This type of retractor has distinct disadvantages in that the central gripping portion thereof is wide and flat and is therefore difficult to delicately manipulate by the practitioner. Further, as the handle portion of this retractor is straight, rather than angular, the hand which normally grips and guides the retractor will necessarily often obstruct the view of the user. Model No. A8540 of the same catalogue shows a retractor which has a long slim tapered handle which allows for easy manipulation by the user. However, as the handle portion is straight, the user's hand will still often block a direct view of the endotracheal tube. Further, the tube engaging portion of this retractor is formed generally in the shape of a common fork, with the tines curled around in order to make a scoop-like shape. For this reason, this retractor is extremely unsuitable for use in the blind technique, as the sharp tips of the tines are liable to engage and tear the tissue surrounding the area adjacent to the endotracheal tube.

The Scanlon-Morris Co. Brochure discloses at pages 2, 3 and 4 thereof a plurality of retractors for general use. The Model No. 86-54 retractor is disclosed as being for tracheal use. However, the design of this tracheal retractor is very similar to the previously mentioned Mueller retractor in that the endotracheal tube-engaging portion is provided with sharp tips, and is therefore of no utility in a blind intubation technique.

The Murray-Baumgartner Surgical Instrument Co. Catalogue (1934) again discloses a plurality of retractors for general surgical use. Of particular interest are the Model Nos. 2149-2152 which display a curved scoop-shaped retractor blade portion. However, it is noted that the handles of these retractors are thin, flat, and of an overall arcuate shape, and therefore have the same disabilities as regards delicate work as do the previously mentioned Mueller retractors.

The Charles Truax Greene & Co. Catalogue depicts a plurality of retractors for use in gynecology. FIG. 7233 of this Catalogue depicts a retractor which has a generally scoop-shaped end. However, the handle of this retractor does not allow the practitioner to grip and manipulate the device in a manner such that the practitioner's hand would not obstruct the view of an endotracheal tube.

The *Journal of the American Medical Association*, July 12, 1952, contains an article on pages 1018 and 1019 thereof which discusses the use of various types of generally S-shaped retractors formed of lucite. However, it is noted that none of the retractors disclosed in this article has a generally scoop-shaped blade attached to a thin elongated generally cylindrical gripping portion.

The most common retractor presently being used for tracheal intubation is the so-called Bearman hook. This device consists of a unitary length of wire formed with a hook at the end thereof. However, this hooked end is disadvantageous in that it has little utility in blind techniques due to the danger of damage to the surrounding tissue. Additionally, the Bearman hook has an inherent flexibility due to its thin wire-like construction, thereby causing difficulties in the lateral manipulation of the endotracheal tube.

SUMMARY OF THE INVENTION

The primary object of the present invention is to provide an improved endotracheal tube retractor having a blunt, generally scoop-shaped blade or tube engaging portion mounted on a handle which facilitates delicate manipulation and good grippability.

Another object of this invention is to provide an endotracheal tube retractor with a portion of the handle thereof inclined at an acute angle with respect to the longitudinal axis of the retractor and which is easily engageable by the fingers of the user in such a manner that the user's hand will not obstruct the view of the endotracheal tube being engaged.

It is a further object of this invention to provide a retractor which facilitates the intubation of patients under direct vision or by using blind techniques.

It is a still further object of the invention to provide a retractor instrument capable of directing the tip of an endotracheal tube into the glottis without trauma to the pharynx.

It is still another object of the invention to guide an endotracheal tube in a blind nasotracheal intubation without the need of flexion, extension or any movement of the head, thereby providing a great advantage in patients with fractures of the cervical spine.

These, together with other objects and advantages which will subsequently become apparent, reside in the details of construction as more fully hereinafter described and claimed, reference being had to the accompanying drawings forming a part hereof wherein like numerals refer to like parts throughout.

BRIEF DESCRIPTION OF THE DRAWINGS

FIG. 1 is a perspective view of the endotracheal tube retractor of the present invention;

FIG. 2 is a perspective view illustrating the retractor as it is gripped by a user; and, FIG. 3 is a diagrammatical illustration of the retractor as it is used in endotracheal intubation.

DETAILED DESCRIPTION OF THE INVENTION

Referring now more specifically to the drawings, the numeral 10 generally designates an endotracheal tube retractor having an angled handle portion 12, a tapered, generally cylindrical midsection 14, and a retractor blade portion 16.

The blade portion 16 is provided with a thin, elongated portion 18 formed integrally therewith for connection to the midsection 14. The blade is formed in a generally scoop-like manner, with the widest portion thereof being situated along a line parallel with the bottom of the "scoop", the blade becoming thinner with distance from the wider portion in both directions.

The bottom 20 of the blade is shaped generally in the form of a hyperboloid, that is, in a shape similar to that of a saddle, the center portion of the blade bottom being depressed in a concave manner. The edges of the blade are smooth and rounded, thereby making the instrument very blunt. This configuration is of great advantage in delicate work, since the instrument has no sharp edges or points which could otherwise injure the tissue surrounding the area of operation. This configuration, of course, is of magnified importance when a "blind" intubation technique is employed. The shape of the blade facilitates the sliding and directing of the tube into the glottis of a patient, the portion of the blade in contact with the tube being substantially friction free due to the "saddle-like" shape. Thus, the blade will engage the tube with substantially a line contact.

The midsection 14 of the tool is formed as a generally cylindrical rod with a slight longitudinal taper in the direction of the blade 16. For ease of handling, grippability and rotation, the generally cylindrical surface may be formed with longitudinal chordal flats extending along the length of the midsection, thereby providing substantially flat surfaces for engagement with the fingers of the user.

The angled handle portion 12 is formed integrally with the midsection 14 and is somewhat less than one half the length of the same. The handle is of a generally rectangular, flat-sided shape, and is tapered toward its upper end. As seen in FIG. 1, the handle joins the midsection in a smooth curve, the side surfaces of the handle being continuous with the chordal flats provided on the midsection 14.

The handle is designed to be gripped by the user as shown in FIG. 2. With the hand in a slightly closed position, the thumb is rested on the top surface 22 of the angled handle 12. The index finger engages the flat bottom portion 24 of the handle between the first and third joints, with the tip of the index finger extending over one of the side surfaces 26. As the retractor is symmetrical, it may be used with equal dexterity with either hand of the user. The handle is so angled that it comfortably rests along the index finger of the user, as described above; the angle being in the range of 40 to 70 degrees with respect to the longitudinal axis of midsection 14.

The middle finger engages the handle on the side opposite that of the index finger, such that the instrument may be firmly held between these two fingers.

The primary advantage of the angled handle is that it allows the practitioner to firmly grip the instrument, while at the same time avoiding the possibility of the hand or fingers obstructing the view of the endotracheal tube, the epiglottis, or the larynx, etc. As seen in FIG. 2, when the instrument is gripped as illustrated, neither the hand nor the fingers protrude further than a plane defined by a top chordal surface 31 of the midsection. Therefore, the practitioner is provided with an excellent, unobstructed view even while the endotracheal tube is being manipulated or adjusted in position.

In operation, as illustrated in FIG. 3, an endotracheal tube 30 is passed through the nose or mouth until the tip is visualized or palpated with the examining finger in the posterior pharynx. The blade of the retractor is passed into the posterior pharynx in the area of the endotracheal tube above the cuff 32 thereof. Then, the retractor handle is shifted in a medial direction, and the blade thereof is passed behind the tube, thus engaging the tube in the scoop-like section of the curved retractor blade. After the tube is engaged in the blade, the direction of the tip of the tube may be changed by slightly moving the handle in an anterior, posterior, lateral or medial direction.

When the direct vision technique is utilized, the tube may be engaged by the instrument under direct vision with the use of a laryngoscope. If the blind technique is used, the retractor blade may be guided by the examining finger. As mentioned previously, the conventional technique of blind intubation well known in the anesthesiology art requires the flexing, extending, or rotation of the head. However, by using the instrument of the present invention, this requirement of movement is obviated, as the direction of the tip of the endotracheal tube may be changed by moving the retractor in a lateral, medial, posterior, or anterior direction. Therefore, the endotracheal tube may be easily manipulated to the anterior side of the glottis, thereby directing the tube toward the trachea rather than the esophagus. This technique of blind endotracheal intubation is especially useful with patients with anatomical deformities, such as a spur on the first cervical vertebra protruding into the nasopharynx, mandibular micrognathia, ankylosis of the temporo-mandibular joint, tumor formation in the posterior pharynx, or extensive mandibular fractures. In conditions such as ankylosing spondylitis and cervical traction where the head is immobilized, endotracheal intubation is facilitated by the use of the retractor.

After the endotracheal tube is successfully passed through the vocal cords and into the trachea of the patient, the retractor may be disengaged from the tube by shifting the retractor handle in a lateral direction so as to release the tube from the blade.

The foregoing is to be considered as illustrative only of the principles of the invention. Further, since numerous modifications and changes will readily occur to those skilled in the art, it is not desired to limit the invention to the exact construction shown and described, and, accordingly, all suitable modifications and equivalents may be resorted to and still fall within the scope of the invention which is limited only as defined in the following claims.

I claim:

1. An endotracheal tube retractor comprising:
   (a) a lower blade portion having a scoop-like portion for engagement with an endotracheal tube, said blade being formed with smooth, blunt edges and having a wider portion at the bottom thereof, said bottom being formed with concave curvature,
   (b) a middle portion connected to said blade at the upper end thereof, said middle portion being of generally cylindrical shape and tapering downwardly toward said blade portion,
   (c) a handle portion connected at the lower end thereof to the upper end of said middle portion, said handle portion being oriented at an acute angle with respect to the longitudinal axis of said middle portion, said handle and said scoop-like portion of said blade extending away from said longitudinal axis of said middle portion in opposite directions, said handle portion being generally in the form of an elongated rectangular solid extending upwardly and away from said middle portion in a smooth continuous manner,
   (d) said handle portion and a top section of said middle portion together forming a gripping portion engageable between several fingers of one hand, such that, when gripped, neither the fingers nor the hand extend substantially beyond a plane defined by a front face of said middle portion, and wherein said handle includes a stabilizing support comprising at least one flat surface adapted to lie substantially along the length of a finger of the user, thereby allowing precise manipulation of the retractor.

2. The endotracheal tube retractor as defined in claim 1, wherein said handle portion is longitudinally tapered toward the upper end thereof.

3. The endotracheal tube retractor as defined in claim 2, wherein said generally cylindrical middle portion is provided with a plurality of chordal flats.

* * * * *